March 24, 1964 R. S. MOORE Plant Pat. 2,383
ROSE
Filed Jan. 12, 1962
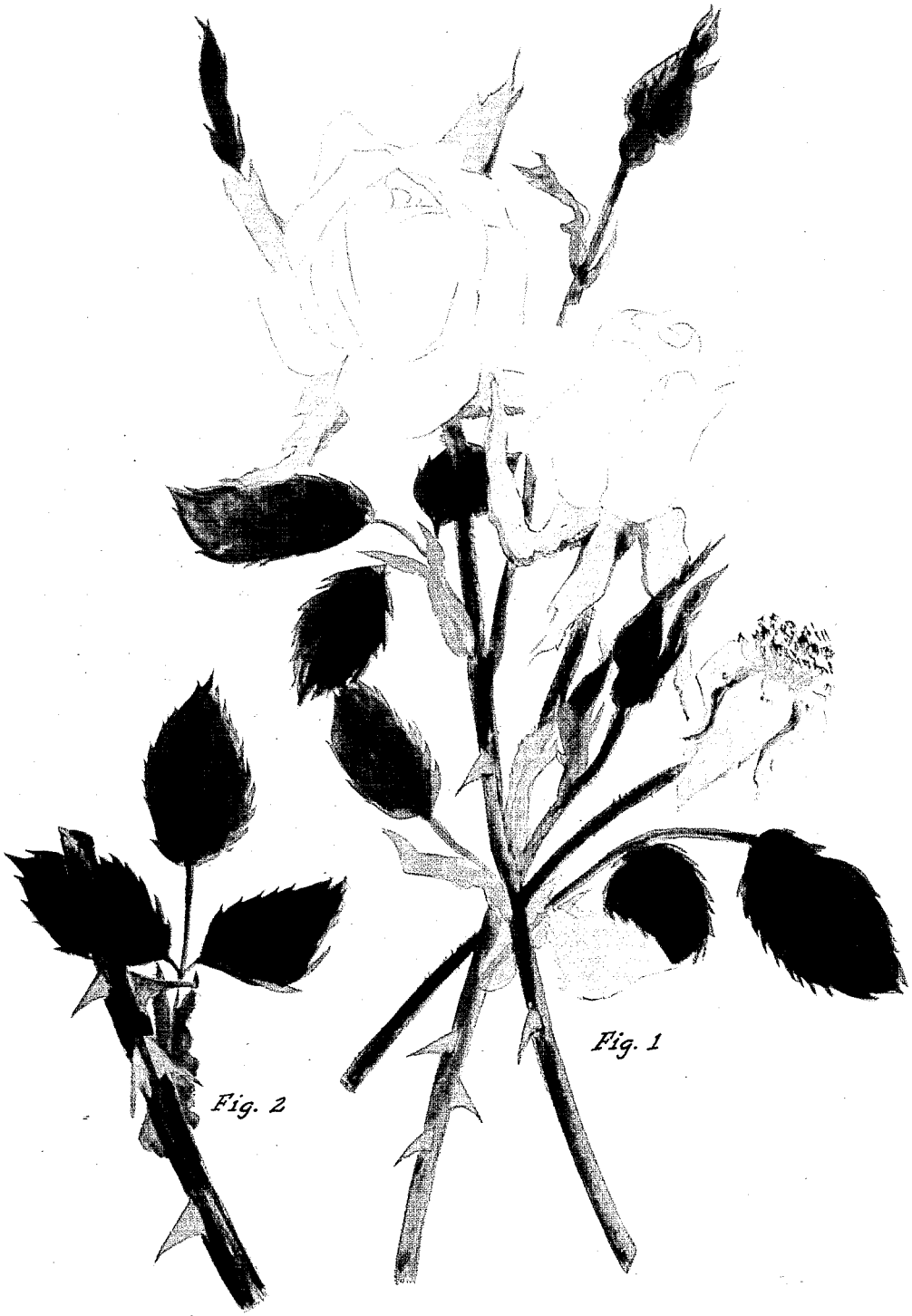
WITNESS
Janette Nunn Copley
INVENTOR
RALPH S. MOORE
ATTORNEYS
Erlitt & Eli 52

United States Patent Office

Plant Pat. 2,383
Patented Mar. 24, 1964

2,383
ROSE

Ralph S. Moore, 2519 E. Mineral King, Visalia, Calif.
Filed Jan. 12, 1962, Ser. No. 165,974
1 Claim. (Cl. Plt.—15)

This invention relates to a new and distinct variety of tall, bush hybrid tea rose plant.

This plant is characterized as to novelty by its vigorous growth habit and hard, mildew-resistant foliage, plus its intense yellow color which does not fade or change appreciably, even in extremely warm or cold weather.

This hybrid tea rose variety resembles its seed parent, Sister Therese (non-patented) in its vigorous growth habit, although its foliage is heavier and better. The new variety of plant is very upright. As the flower opens, the petals turn back (or quill) to give somewhat the effect of a hybrid cactus dahlia. The petal edges roll downward, making them look quite pointed.

The yellow color of this new variety of hybrid tea rose plant is so intense that if buds or flowers are picked and allowed to dry, the dried petals remain very yellow instead of fading. The bright yellow color holds well until the petals drop, even in warm summer weather; in really cool weather the yellow coloring at the base of the bud and flower may show some light green.

This new variety of hybrid tea rose plant was originated by me, in my nursery located at Visalia, California, and under conditions of careful control and observation, as a cross between Sister Therese (hybrid tea) (not patented) as the seed parent and Julien Potin (hybrid tea) (not patented) as the pollen parent. Subsequent to origination of the variety, I successfully asexually reproduced it in my nursery, located as aforesaid, by budding as well as cuttings, the reproductions having run true in all respects.

The drawing illustrates the variety including foliage, buds and flowers.

Referring now specifically to the new and distince variety of hybrid tea rose plant, the following is a detailed description thereof in outline, all major color plate identifications being to the British Colour Council Horticultural Colour Chart, except where common terms of color definition are employed.

Type: Tall; bush-type; hardy; greenhouse or outdoor; seedling; cut flowers; garden decoration.
Class: Hybrid tea.

*Flowers*

Continuity: Intermittent to continuous.
Fragrance: Strong; sweet; tea or fruit.
Flowers borne: Singly; sometimes in candelabra manner atop very vigorous shoots, as seed parent, Sister Therese.
Quantity of bloom: Free; outdoors or greenhouse.
Bud:
- *Penduncle.*—Long; slender; of medium weight; erect; medium green; numerous green prickles.
- *Before calyx breaks.*—Size—large. Form—long and pointed, with foliaceous appendages on the surface of the bud; with foliaceous parts extending beyond the tip of the bud equal to one-fourth or more of its length. Color—green.
- *As calyx breaks.*—Color—greenish yellow.
- *As first petal opens.*—Size—large. Form—pointed; ovoid. Color: outside—Lemon Yellow 4/1 shading to lighter lemon yellow 4/2; inside—Aureolin Yellow 3 or 3/1 shading to lighter Aureolin yellow 3/2 or 3/3. Opening—opens well.

Bloom:
- *Size when fully opened.*—Large, 4" to 4½".

- *Petalage.*—Double to very double; from 30 to 50 petals arranged irregularly.
- *Form.*—Full, high center at first; becoming high centered and globular; petals remaining at first very loosely rolled outward; becoming later loosely rolled outward.

Petals: Thick; leathery; inside satiny, outside satiny.
- *Shape.*—Outside—Obovate with acute tip. Intermediate—obovate with acute tip. Inside—lanceolate.
- *Color.*—Newly opened flower from plant grown outdoors (September)—Outside petal: outside surface—Aureolin Yellow 3/1 shading to Canary Yellow 2/2; inside surface—Aureolin Yellow 3/1 to 3/2 shading to Canary yellow 2/2. Intermediate petal: outside surface—Canary Yellow 2/2; inside surface—Canary Yellow 2/2. Inner petal: outside surface—Canary Yellow 2/2; inside surface—Canary Yellow 2/2. Rose opened for three days outdoors (September)—Outside petal: outside surface—Canary Yellow 2/2 to 2/3; inside surface—Canary Yellow 2/2 to 2/3. Inside petal: outside surfaces and inside surfaces same as outside petal.
- *General color effect.*—Newly opened flower, bright yellow. Three days open, softer yellow.
- *Behavior.*—Drop off cleanly; usually do well in any weather.
- *Flower longevity.*—Three to five days on bush in garden (September). Three to four days as cut roses grown outdoors, kept at living room temperatures (September).

Reproductive organs:
- *Stamens.*—Medium number; arranged irregularly about pistils.
- *Filaments.*—Medium to long; yellow; most with anthers.
- *Anthers.*—Medium size; yellow; all open at once.
- *Pollen.*—Moderate amount; yellow.
- *Pistils.*—Medium number.
- *Styles.*—Uneven; short; medium size; bunched.
- *Stigma.*—Yellow.
- *Ovaries.*—All enclosed in calyx.
- *Hips.*—Globular; reddish; moderately smooth; walls thick and fleshy.
- *Sepals.*—Permanent; long; spear shaped and recurved; brown.
- *Seeds.*—Few; large.

*Plant*

Foliage:
- *Leaves.*—Compound of 5 leaflets; of normal number; large; heavy; leathery; glossy.
- *Leaflets.*—Shape—lanceolate; apex—acute; base—round; margin—serrate.
- *Color.*—Mature: upper surface—normal green; under surface—normal green. Young: upper surface—normal green; under surface—normal green.
- *Rachis.*—Medium; upper side grooved and hairy; under side sparsely thorny.
- *Stipules.*—Medium length; medium width; moderately short points, turning out at an angle of about 45° toward the stem.
- *Disease.*—Resistant to mildew as compared with other varieties grown under comparable cultural conditions at Visalia, California.

Growth:
- *Habit.*—Bushy; upright; branched.
- *Growth.*—Medium.
- *Canes.*—Medium weight.

*Main stems.*—Color—green, turn brown with age. Thorns—several, medium to long, hooked downward, with long, broad base. Prickles—none to few. Hairs—none to few.

*Branches.*—Color—green. Thorns—several, of medium length, hooked downward, with long, rounded base. Prickles—few, green to brown. Hairs—none to few.

*New shoots.*—Color—bright green. Thorns—few, hooked downward, with narrow, rounded base. Prickles—none to few, green. Hairs—none.

The following is claimed:

A new and distinct variety of hybrid tea rose plant, substantially as herein shown and described of the tall, bush-type, outdoor or greenhouse variety characterized by its upright stature, by its vigorous growth habit which resembles its seed parent, Sister Therese, by its hard, mildew-resistant foliage, by large, thick, pointed, leathery petals arranged irregularly, being bright yellow when first opened and a softer yellow after being open for three days, its intense yellow color holding well in all types of weather.

No references cited.